(12) United States Patent
Tateishi et al.

(10) Patent No.: US 8,465,819 B2
(45) Date of Patent: Jun. 18, 2013

(54) DRUG SOLUTION CONTAINER PACKAGE AND METHOD FOR MANUFACTURING THE SAME

(75) Inventors: Isamu Tateishi, Naruto (JP); Hitoshi Mori, Tokushima (JP); Yasushi Morimoto, Naruto (JP)

(73) Assignee: Otsuka Pharmaceutical Factory, Inc., Tokushima (JP)

( * ) Notice: Subject to any disclaimer, the term of this patent is extended or adjusted under 35 U.S.C. 154(b) by 867 days.

(21) Appl. No.: 11/911,644

(22) PCT Filed: Apr. 19, 2006

(86) PCT No.: PCT/JP2006/308206
§ 371 (c)(1),
(2), (4) Date: Oct. 15, 2007

(87) PCT Pub. No.: WO2006/118034
PCT Pub. Date: Nov. 9, 2006

(65) Prior Publication Data
US 2009/0032426 A1    Feb. 5, 2009

(30) Foreign Application Priority Data
Apr. 28, 2005    (JP) .................. 2005-132624

(51) Int. Cl.
| | |
|---|---|
| B32B 1/02 | (2006.01) |
| B32B 27/08 | (2006.01) |
| B32B 27/30 | (2006.01) |
| B32B 27/32 | (2006.01) |
| B32B 27/36 | (2006.01) |
| B65D 85/84 | (2006.01) |
| A61L 2/08 | (2006.01) |
| A61L 2/18 | (2006.01) |
| B65B 29/00 | (2006.01) |
| B65B 55/04 | (2006.01) |
| B65B 31/00 | (2006.01) |

(52) U.S. Cl.
USPC .......... 428/35.7; 428/36.6; 428/36.7; 422/26; 422/28; 206/524.6; 53/400; 53/426; 53/433

(58) Field of Classification Search
USPC ................. 428/34.1, 35.7, 36.6, 36.7, 36.9, 428/36.91, 36.92; 206/528–540, 524.1, 524.6; 422/1, 26, 38, 27, 28; 53/400, 426, 433
See application file for complete search history.

(56) References Cited

U.S. PATENT DOCUMENTS
4,414,230 A * 11/1983 Hanabata et al. ............. 426/106
(Continued)

FOREIGN PATENT DOCUMENTS
CN    1218385 A    6/1999
(Continued)

OTHER PUBLICATIONS
Decision to Grant; Japanese Appln. 2011-172243, Dec. 6, 2012, pp. 1-3.

*Primary Examiner* — Walter B Aughenbaugh
(74) *Attorney, Agent, or Firm* — Finnegan, Henderson, Farabow, Garrett & Dunner, L.L.P.

(57) ABSTRACT

A drug solution container package, which can restrain degradation of a drug solution, proliferation of microbes, etc. accompanying the transmission of oxygen in a high degree while maintaining characteristics required of plastic drug solution containers such as heat resistance, impact resistance, pliability, transparency, and resistance against elution of plastic forming material, and to provide a method for manufacturing the drug solution container package. A drug solution is first contained and sealed in a plastic drug solution container having an oxygen gas transmission rate (25° C., 60% RH) of not less than 200 $cm^3/m^2 \cdot 24$ h·atm within twelve hours after being subject to steam or hot water sterilization, and having an oxygen gas transmission rate (25° C., 60% RH) of not more than 100 $cm^3/m^2 \cdot 24$ h·atm when the oxygen gas transmission rate is in a steady state, and thereafter the plastic drug solution container is steam sterilized or hot water sterilized and then contained and sealed along with an oxygen scavenger in an outer pouch having an oxygen barrier property.

14 Claims, 5 Drawing Sheets

U.S. PATENT DOCUMENTS

| | | |
|---|---|---|
| 5,032,632 A | 7/1991 | Saxton |
| 5,132,149 A | 7/1992 | Kotani et al. |
| 5,728,681 A | 3/1998 | Kido et al. |
| 5,766,751 A * | 6/1998 | Kotani et al. ............... 428/323 |
| 5,772,960 A | 6/1998 | Ito et al. |
| 6,007,529 A | 12/1999 | Gustafsson et al. |
| 6,398,771 B1 | 6/2002 | Gustafsson et al. |
| 6,713,137 B1 * | 3/2004 | Andersson et al. ........ 428/35.7 |
| 6,996,995 B2 | 2/2006 | Voute et al. |
| 2002/0192411 A1 * | 12/2002 | Kai et al. ................... 428/35.7 |
| 2004/0050744 A1 | 3/2004 | Hama et al. |
| 2005/0177128 A1 | 8/2005 | Nagao et al. |
| 2006/0229583 A1 | 10/2006 | Nagao et al. |

FOREIGN PATENT DOCUMENTS

| | | |
|---|---|---|
| CN | 1582112 A | 2/2005 |
| JP | 2-200266 A | 8/1980 |
| JP | 63-275346 | 11/1988 |
| JP | 2-258339 | 10/1990 |
| JP | 4-146142 A | 5/1992 |
| JP | 4-276253 | 10/1992 |
| JP | 5-031154 A | 2/1993 |
| JP | 5-064653 A | 3/1993 |
| JP | 7-67936 A | 3/1995 |
| JP | 9-182778 A | 7/1997 |
| JP | 10-80464 | 3/1998 |
| JP | 10-201818 | 8/1998 |
| JP | 11-285520 | 10/1999 |
| JP | 2000-33674 | 2/2000 |
| JP | 2002-160771 | 6/2002 |
| JP | 2002-173171 | 6/2002 |
| JP | 2003-10287 | 1/2003 |
| JP | D1177640 | 6/2003 |
| JP | 2003-205014 | 7/2003 |
| JP | 2005-152618 | 6/2005 |
| JP | 2005-523772 | 8/2005 |
| JP | 2005-304911 | 11/2005 |
| JP | 2006-020657 | 1/2006 |
| JP | 2006-187429 | 7/2006 |
| JP | 2006-217975 | 8/2006 |
| WO | WO 88/08694 A | 11/1988 |
| WO | WO 01-62202 A1 | 8/2001 |
| WO | WO 03/018312 A1 | 3/2003 |
| WO | WO 03/037083 A1 | 5/2003 |
| WO | WO 03/092574 A1 | 11/2003 |
| WO | WO 2004/093775 | 1/2005 |
| WO | WO 2005/004902 | 1/2005 |

* cited by examiner

DRUG SOLUTION CONTAINER PACKAGE AND METHOD FOR MANUFACTURING THE SAME

TECHNICAL FIELD

This invention relates to a drug solution container package, arranged by making a drug solution container, which is sealed after being filled with a drug solution, contained and sealed in an outer pouch, and a method for manufacturing this drug solution container package.

BACKGROUND ART

In recent years, plastic containers, which are lightweight, pliable, good in handling properties, and readily disposable, are widely used as containers for containing drug solutions, and as a plastic that forms such a plastic container, polyethylene, polypropylene, or other polyolefin is often used from the standpoint of stability with respect to drug solutions and medicinal safety.

However, due to being a material of a high oxygen gas transmission rate, polyolefins are not necessarily suitable in applications of containing and preserving drug solutions that readily undergo oxidative decomposition from the standpoint of quality maintenance of drug solutions, etc.

On the other hand, Patent Document 1 describes a package for infusion in which an infusion, made up of an aqueous solution containing amino acids, is filled in a primary medical container that has a gas transmitting property, and the infusion, filled in the primary medical container, is then contained along with an oxygen scavenger in a secondary packaging container that is substantially impermeable to oxygen.

Also, Patent Document 2 describes a drug solution container film having an inorganic compound film formed on at least one side of a plastic film and having the following physical properties (1) through (4):
(1) an oxygen gas transmission rate of not more than 1 cc/m$^2$·24 hr·atm;
(2) a moisture transmission rate of not more than 1 g/m$^2$·24 hr·atm;
(3) a light transmittance of not less than 80%; and
(4) a hue b value of not more than 5.

Further, Patent Document 3 describes an infusion container having a gas barrier property and formed of a resin container having a flexible wall and at least an outlet formed therein, and in which the above-mentioned container wall is formed of multiple layers that are divided into an inner layer and an outer layer with an intermediate layer of polyvinyl alcohol as a boundary, the above-mentioned innermost layer is a polyolefin layer with a thickness in a range of 50 to 800 μm, and the above-mentioned outer layer is provided so that the above-mentioned outer layer has a moisture transmission amount So (g/m$^2$·24 hrs at a temperature of 40° C. and 90% RH) of not less than twice a moisture transmission amount Si (g/m$^2$·24 hrs at a temperature of 40° C. and 90% RH) of the above-mentioned inner layer; and describes an infusion container, in which the above-described container is packaged along with a drying agent inside a package. The same document also describes that, in the above-described infusion container, the gas barrier property of the container wall recovers immediately even after performing autoclave sterilization.

Patent Document 1: Japanese Unexamined Patent Publication No. 63-275346
Patent Document 2: Japanese Unexamined Patent Publication No. 11-285520
Patent Document 3: Japanese Unexamined Patent Publication No. 10-80464

DISCLOSURE OF THE INVENTION

Problem to be Solved by the Invention

When, as in the invention described in Patent Document 1, the primary container is oxygen gas transmissible, however, oxidative degradation of the solution contained in the primary container cannot be prevented if the primary container is left standing after the secondary container is opened. Moreover, if microbes, etc., become mixed into the drug solution by error when another drug solution is mixed into the primary container from the exterior, proliferation of microbes may be accelerated by the transmission of oxygen into the primary container from the exterior.

Meanwhile, as examples of a film of a plastic provided with an oxygen barrier property (referred to herein after simply as "oxygen barrier plastic"), plastic films using inorganic materials, such as plastic films on which silica or alumina is vapor deposited and plastic films on which an aluminum film is laminated, have been known.

However, in a drug solution container formed using an oxygen barrier plastic film such as in the invention described in Patent Document 2, because of the excellent oxygen barrier property of the above-mentioned film, it is inevitable that the contents undergo oxidative degradation with time or microbes erroneously mixed into the drug solution proliferate if the drug solution container is sealed with oxygen being contained in a head space thereof. It thus becomes necessary to perform a process of lowering an amount of dissolved oxygen in a drug solution before filling and sealing the drug solution in the drug solution container and a process of replacing the above-mentioned head space with nitrogen or other inert gas and bringing the replacement rate infinitely close to 100%. This causes manufacturing equipment to become large and complex and leads to increased cost. Moreover, in the above-mentioned oxygen barrier plastic, pinholes may form due to impacts resulting from vibration during transport, etc.

Further, as plastics with an oxygen barrier property, polyvinylidene chloride, polyacrylonitrile, polyvinyl alcohols, ethylene-vinyl alcohol copolymers, etc., are known, and films formed from such plastics are also supplied.

However, because these plastic films are not adequate in heat resistance, impact resistance, pliability, transparency, etc., are not suitable for incineration disposal, or may give rise to eluted matter upon contact with a drug solution, they cannot be used appropriately as they are to form drug solution containers. In particular, polyvinyl alcohols and ethylene-vinyl alcohol copolymers have the problem of changing greatly in oxygen barrier property depending on a change in humidity.

Meanwhile, though Patent Document 3 describes that the gas barrier property of the infusion container recovers immediately after autoclave sterilization, because no consideration is made on oxygen present inside the infusion container, the issues of oxidative degradation of the contents with time, proliferation of microbes, etc., are not resolved.

An object of this invention is thus to provide a drug solution container package, in which degradation of a drug solution, proliferation of microbes, etc. accompanying the transmission of oxygen can be restrained in a high degree while maintaining characteristics required of plastic drug solution containers, such as heat resistance, impact resistance, pliability, transparency, and resistance against elution of plastic forming material; and to provide a method for manufacturing the drug solution container package.

Means for Solving the Problem

In order to achieve the above object, this invention provides:

(1) a drug solution container package comprising: a plastic drug solution container in which a drug solution is contained and sealed and which is steam sterilized or hot water sterilized; an oxygen scavenger; and an outer pouch with an oxygen barrier property for containing and sealing the above-mentioned plastic drug solution container and the above-mentioned oxygen scavenger, wherein a plastic forming the plastic drug solution container has an oxygen gas transmission rate of not less than 200 $cm^3/m^2 \cdot 24$ h·atm at a temperature of 25° C. and a humidity of 60% RH within twelve hours after steam sterilization or hot water sterilization and has an oxygen gas transmission rate of not more than 100 $cm^3/m^2 \cdot 24$ h·atm at a temperature of 25° C. and a humidity of 60% RH when the oxygen gas transmission rate is in a steady state;

(2) a drug solution container package according to (1), in which the above-mentioned steam sterilization is a process of heating the above-mentioned plastic drug solution container for 10 to 60 minutes under an inert gas atmosphere of a temperature of 100 to 121° C. in a steam saturated state;

(3) a drug solution container package according to (1), wherein the plastic forming the above-mentioned plastic drug solution container is a multilayer film having a sealing layer formed of a polyolefin-based plastic at an inner surface side of the above-mentioned plastic drug solution container, a protective layer on an outer surface side of the above-mentioned plastic drug solution container, and an intermediate layer formed of a polyol-based plastic between the above-mentioned sealing layer and the above-mentioned protective layer.

(4) a drug solution container package according to (3), wherein the polyol-based plastic forming the above-mentioned intermediate layer is an ethylene-vinyl alcohol copolymer with an ethylene content of 10 to 45 mole %;

(5) a drug solution container package according to (3), wherein, of the above-mentioned multilayer film, a water vapor transmission rate of the entirety of layers disposed at the outer surface side of the above-mentioned plastic drug solution container with respect to the above-mentioned intermediate layer is 1 to 50 $g/m^2 \cdot 24$ h at a temperature of 25° C. and a humidity of 90% RH;

(6) a drug solution container package according to (3), wherein the above-mentioned multilayer film furthermore has a low water absorption layer, formed of a low water absorption plastic, between the above-mentioned sealing layer and the above-mentioned intermediate layer;

(7) a drug solution container package according to (6), wherein the above-mentioned low water absorption plastic is a cyclo olefin polymer;

(8) a drug solution container package according to (1), wherein the plastic forming the above-mentioned plastic drug solution container has an oxygen gas transmission rate of 500 to 100 $cm^3/m^2 \cdot 24$ h·atm at a temperature of 25° C. and a humidity of 60% RH within twelve hours after being subjected to steam sterilization or hot water sterilization;

(9) a drug solution container package according to (1), wherein the plastic forming the above-mentioned plastic drug solution container has an oxygen gas transmission rate of 0.5 to 70 $cm^3/m^2 \cdot 24$ h·atm at a temperature of 25° C. and a humidity of 60% RH when the oxygen gas transmission rate is in a steady state;

(10) a drug solution container package according to (1), wherein the above-mentioned plastic drug solution container is formed of such a plastic that requires at least two days for the oxygen gas transmission rate to attain the steady state after steam sterilization or hot water sterilization;

(11) a drug solution container package according to (1), wherein a drug solution contained and sealed in the above-mentioned plastic drug solution container is a drug solution that contains a readily oxidized substance;

(12) a drug solution container package according to (1), wherein the above-mentioned outer pouch has a water vapor transmission rate of 0.5 to 30 $g/m^2 \cdot 24$ h at a temperature of 25° C. and a humidity of 90% RH;

(13) a method for manufacturing a drug solution container package wherein after making a drug solution contained and sealed in a plastic drug solution container formed of a plastic having an oxygen gas transmission rate of not less than 200 $cm^3/m^2 \cdot 24$ h·atm at a temperature of 25° C. and a humidity of 60% RH within twelve hours after steam sterilization or hot water sterilization and having an oxygen gas transmission rate of not more than 100 $cm^3/m^2 \cdot 24$ h·atm at a temperature of 25° C. and a humidity of 60% RH when the oxygen gas transmission rate is in a steady state, the plastic drug solution container is steam sterilized or hot water sterilized, and then the steam-sterilized or hot-water-sterilized plastic drug solution container and an oxygen scavenger are contained and sealed in an outer pouch having an oxygen barrier property;

(14) a method for manufacturing a drug solution container package according to (13), wherein the above-mentioned steam sterilization is a process of heating the above-mentioned plastic drug solution container for 10 to 60 minutes under an inert gas atmosphere of a temperature of 100 to 121° C. in a steam saturated state;

(15) a method for manufacturing a drug solution container package according to (13), wherein the above-mentioned outer pouch has a water vapor transmission rate of 0.5 to 30 $g/m^2 \cdot 24$ h at a temperature of 25° C. and a humidity of 90% RH; and

(16) a method for manufacturing a drug solution container package according to (13), wherein before the above-mentioned plastic drug solution container and the above-mentioned oxygen scavenger are contained and sealed in the above-mentioned outer pouch, a space between the above-mentioned plastic drug solution container and the above-mentioned outer pouch is replaced with an inert gas.

In this invention, an oxygen gas transmission rate ($O_2GTR$) of a plastic is measured according to Method B (Equal Pressure Method) defined in JIS K $7126_{-1987}$ "Testing Method for Gas Transmission Rate through Plastic Film and Sheeting," and a water vapor transmission rate of a plastic is measured according to A method (Humidity sensor method) defined in JIS K $7129_{-1992}$ "Testing methods for water vapor transmission rate of plastic film and sheet (instrument method)."

In this invention, the following are defined as oxygen gas transmission rates of the plastic that forms the plastic drug solution container:

(a) a value measured after subjecting the plastic to steam sterilization [heating under an atmosphere in a steam saturated state; steam sterilization, or high-pressure steam sterilization (autoclave), for example] or hot water sterilization (hot water shower sterilization or hot water spray sterilization, for example) and removing water attached to the surface of the steam-sterilized or hot-water-sterilized plastic and letting the plastic stand to cool, at a temperature of 25° C. and a humidity of 60% RH (generally, an environment of a room temperature and relatively moderate humidity) within twelve hours after steam sterilization or hot water sterilization; and (b) a value measured at a temperature of 25° C. and a humidity of 60% RH in the state in which a variation with time of an oxygen gas transmission rate is no longer observed, that is, the oxygen gas transmission rate is in a steady state.

The above-mentioned oxygen gas transmission rate is preferably the value measured within eight hours after the steam sterilization or hot water sterilization and more preferably the value measured within six hours after the steam sterilization or hot water sterilization. Normally an elapse of approximately four hours is required for a temperature of a plastic subjected to steam sterilization or hot water sterilization to drop to the oxygen gas transmission rate measurement temperature of 25° C. by letting the plastic stand to cool.

Also, the above-mentioned steam sterilization or hot water sterilization is preferably performed at atmospheric pressure or under a pressurized atmosphere of a barometric pressure of not more than 4000 hPa and more preferably performed under a pressurized atmosphere of a barometric pressure of 2000 to 3500 hPa.

The above-mentioned steady state refers to a state in which a variation with time of an oxygen gas transmission rate (an oxygen gas transmission rate measured under fixed conditions, such as a temperature of 25° C. and a humidity of 60% RH) is within ±5% per hour and more preferably within ±3% per hour.

Normally, to return an oxygen gas transmission rate of a plastic used for forming a drug solution container to the steady state after steam sterilization or hot water sterilization by letting the plastic stand to cool, an elapse of two days, preferably three days, and more preferably four days, after steam sterilization or hot water sterilization is required in general.

Effect of the Invention

Because the plastic drug solution container of the drug solution container package according to this invention is formed of a so-called low oxygen gas transmission plastic with an oxygen gas transmission rate of not more than 100 $cm^3/m^2 \cdot 24$ h·atm under the environment of a temperature of 25° C. and a humidity of 60% RH when the oxygen gas transmission rate is in the steady state, even when the drug solution container is left standing after opening the outer pouch of the above-mentioned drug solution container package, according to this invention, transmission of oxygen into the drug solution container can be restrained to prevent oxidative degradation of the drug solution contained in a drug solution container.

Also, the plastic forming the above-mentioned plastic drug solution container has an oxygen gas transmission rate of not less than 200 $cm^3/m^2 \cdot 24$ h·atm at a temperature of 25° C. and a humidity of 60% RH after the steam sterilization or hot water sterilization, and exhibits an extremely high oxygen gas transmission in comparison to when the oxygen gas transmission rate is in the steady state. Moreover, the oxygen gas transmission rate of the plastic after steam sterilization or hot water sterilization normally does not return rapidly to the state before the steam sterilization or hot water sterilization. Thus, with the method for manufacturing the drug solution container package according to this invention, in which the drug solution container subjected to the steam sterilization or hot water sterilization is contained and sealed along with the oxygen scavenger in the outer pouch with the oxygen barrier property before the oxygen gas transmission rate of the plastic drops significantly, the oxygen that remains inside the above-mentioned drug solution container (for example, the oxygen remaining in the head space of the drug solution container and the dissolved oxygen in the drug solution) can be removed from inside the drug solution container.

Thus, with the above-described drug solution container package and the method for manufacturing the same, oxidative degradation of the drug solution contained in a drug solution container can be restrained in a high degree. Moreover, even when a small amount of microbes become mixed into a drug solution by error, proliferation of the microbes can be restrained in a high degree.

Figure 1:
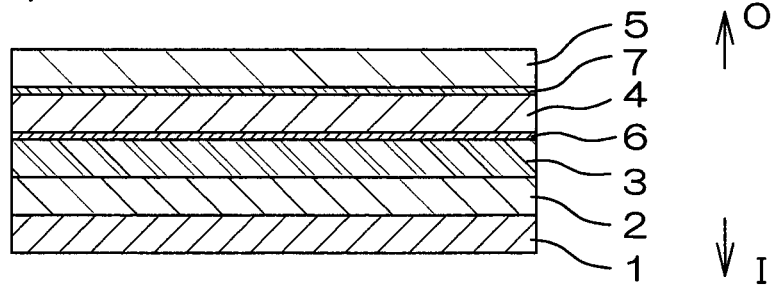
FIG. 1 is a schematic sectional view of an embodiment of a plastic that forms a plastic drug solution container.

| Description of the Numerals | |
|---|---|
| 1 | sealing layer |
| 4 | intermediate layer |
| 5 | protective layer |
| 10 | plastic drug solution container |

MODES FOR CARRYING OUT THE INVENTION

A drug solution container package according to this invention includes: a plastic drug solution container, in which a drug solution is contained and sealed and which is steam sterilized or hot water sterilized; an oxygen scavenger; and an outer pouch for containing and sealing the above-mentioned plastic drug solution container and the above-mentioned oxygen scavenger.

In the drug solution container package according to this invention, the plastic drug solution container is formed of a plastic having an oxygen gas transmission rate of not less than 200 $cm^3/m^2 \cdot 24$ h·atm at a temperature of 25° C. and a humidity of 60% RH within twelve hours after steam sterilization or hot water sterilization, and having an oxygen gas transmission rate of not more than 100 $cm^3/m^2 \cdot 24$ h·atm at a temperature of 25° C. and a humidity of 60% RH when the oxygen gas transmission rate is in the steady state.

Particularly in the above-mentioned range, the oxygen gas transmission rate of the above-mentioned plastic at a temperature of 25° C. and a humidity of 60% RH within twelve hours after steam sterilization or hot water sterilization is preferably not less than 500 $cm^3/m^2 \cdot 24$ h·atm, more preferably not less than 700 $cm^3/m^2 \cdot 24$ h·atm, and even more preferably 700 to 1000 $cm^3/m^2 \cdot 24$ h·atm.

In the above-mentioned plastic, when the oxygen gas transmission rate at a temperature of 25° C. and a humidity of 60% RH within twelve hours after steam sterilization or hot water sterilization falls below the above-mentioned range, the effect of removing the oxygen contained in the head space of the plastic drug solution container, the dissolved oxygen in the drug solution, etc. from the drug solution container to the exterior is lowered after performing steam sterilization or hot water sterilization on the plastic drug solution container, which reduces the effect of restraining and preventing oxidative degradation of a drug solution. Meanwhile, though the upper limit of the oxygen gas transmission rate after steam sterilization or hot water sterilization is not restricted in particular, the upper limit is approximately 1000 cm$^3$/m$^2$·24 h·atm in terms of the properties of a plastic used in a plastic drug solution container.

Particularly in the above-mentioned range, the oxygen gas transmission rate of the above-mentioned plastic at a temperature of 25° C. and a humidity of 60% RH when the oxygen gas transmission rate is in the steady state is preferably not more than 70 cm$^3$/m$^2$·24 h·atm, more preferably not more than 30 cm$^3$/m$^2$·24 h·atm, and even more preferably 0.5 to 10 cm$^3$/m$^2$·24 h·atm.

If the oxygen gas transmission rate of the above-mentioned plastic at a temperature of 25° C. and a humidity of 60% RH when the oxygen gas transmission rate is in the steady state exceeds the above-mentioned range, the transmission of oxygen into the drug solution container cannot be restrained when the above-mentioned drug solution container is left standing after the outer pouch of the drug solution container package is opened, for example, and this brings about oxidative degradation of a drug solution contained in the drug solution container. On the other hand, though the lower limit of the oxygen gas transmission rate when the oxygen gas transmission rate is in the steady state is preferably zero, the lower limit is preferably approximately 0.5 cm$^3$/m$^2$·24 h·atm in terms of the properties of the plastic used in the plastic drug solution container. The lower limit of the oxygen gas transmission rate can also be approximately 1 cm$^3$/m$^2$·24 h·atm or approximately 5 cm$^3$/m$^2$·24 h·atm.

As mentioned above, the oxygen gas transmission rate of the plastic is the oxygen gas transmission rate (O$_2$GTR) measured according to Method B (Equal Pressure Method) defined in JIS K7126$_{-1987}$ "Testing Method for Gas Transmission Rate through Plastic Film and Sheeting." Examples of measuring equipment used for measuring the oxygen gas transmission rate include a product of the trade name "OX-TRAN (registered trademark)" made by MOCON, Inc., and a product of the trade name "OPT-5000" made by Lyssy AG.

The process conditions of the steam sterilization or hot water sterilization performed on the plastic drug solution container are not restricted in particular and may be set as suited according to general process conditions for sterilization of containers containing a drug solution, and specifically, for example, according to a type and amount of a drug solution contained, a material quality and thickness of a plastic that forms the container, and other conditions as well as in consideration that the sterilization of the drug solution fits to the predetermined conditions.

In general, the steam sterilization is carried out in an atmosphere of a temperature of 100 to 121° C. and in a steam saturated state for a heating time of 10 to 60 minutes. Though the pressurization condition during the steam sterilization is not restricted in particular, the steam sterilization is preferably performed at atmospheric pressure or under a pressurized atmosphere of a barometric pressure of not more than 4000 hPa and more preferably performed under a pressurized atmosphere of a barometric pressure of 2000 to 3500 hPa.

On the other hand, the hot water sterilization may be performed under conditions conforming to conventional conditions or the conditions of the steam sterilization by, for example, injecting or spraying hot water of about 100 to 120° C., for 10 to 60 minutes at atmospheric pressure or under a pressurized atmosphere.

The steam sterilization or hot water sterilization is preferably performed under an inert gas atmosphere. In this case, the head space of the drug solution container prior to being contained and sealed in the outer pouch can be replaced in some degree by the above-mentioned inert gas during the steam sterilization or hot water sterilization, and the amount of oxygen contained in the drug solution container prior to being contained and sealed in the outer pouch can be lessened in advance. Also, an amount of oxygen scavenger necessary for removing the oxygen in the drug solution container after containing and sealing the drug solution container in the outer pouch and time required for the deoxygenation process can be lessened, and the effects of restraining and preventing the oxidative degradation of a drug solution can be improved further.

Though the above-mentioned inert gas is not restricted in particular, it is preferably a gas, such as nitrogen, argon, etc., that does not readily cause (or that prevents) oxidation and other alterations of a drug solution.

In the plastic that forms the plastic drug solution container, the oxygen gas transmission rate after the steam sterilization or hot water sterilization and the oxygen gas transmission rate in the steady state can be set respectively to suitable values by changing the type, thickness, etc. of the above-mentioned plastic, or by changing a layer arrangement, thickness, etc. in the case where the above-mentioned plastic is a multilayer film.

In regard to the oxygen gas transmission rate of the plastic that forms the plastic drug solution container, in order to provide a significant difference between a value of the oxygen gas transmission rate after the steam sterilization or hot water sterilization and a value of the oxygen gas transmission rate in the steady state, use of a polyol-based plastic as the plastic that forms the drug solution container is preferable, for example.

Ethylene-vinyl alcohol copolymers can be cited as examples of the polyol-based plastic, although the polyol-based plastic is not restricted thereto.

In particular, an ethylene-vinyl alcohol copolymer with an ethylene content of 10 to 45 mole % can be cited as a preferable example.

When the ethylene content of the ethylene-vinyl alcohol copolymer falls below 10 mole %, it may not be possible, for example, to secure an adequate water resistance for withstanding the steam sterilization or hot water sterilization. Also, it may not be possible that the oxygen gas transmission rate increased by the steam sterilization or hot water sterilization returns to the original value even after a temperature of the plastic is lowered.

On the other hand, when the ethylene content of the ethylene-vinyl alcohol copolymer exceeds 45 mole %, whitening occurs due to the steam sterilization or hot water sterilization and transparency of the container thus drops significantly. Also, the oxygen gas transmission rate in the steady state may exceed the above-mentioned range under the conditions of the temperature of 25° C. and humidity of 60% RH, and consequently, it may not be possible to restrain the transmission of oxygen into the drug solution container when, for example, the above-mentioned drug solution container is left standing after the outer pouch of the drug solution container package is opened. Particularly in the above-mentioned range, the above-mentioned ethylene content is preferably 25 to 35 mole %.

For the purpose of improving the heat resistance of the drug solution container, a polyamide-based resin (such as nylon-6, etc.) or a phosphorus-based antioxidant [for example, tris(2,4-di-t-butylphenyl) phosphate], for example, may be blended into the above-mentioned polyol-based plastic, if needed. A blending amount of such a polyamide-based resin or phosphorus-based antioxidant may be set within a range in which a drug solution contained in the drug solution container is not affected.

From the standpoint of maintaining basic properties as a drug solution container, the plastic that forms the plastic drug solution container is preferably a plastic film with a multilayer structure having a polyol-based plastic as an intermediate layer, a sealing layer (innermost layer) formed of a polyolefin-based plastic at an inner surface side of the drug solution container with respect to the intermediate layer, and a protective layer (outermost layer) on an outer surface side of the drug solution container with respect to the intermediate layer.

When, for example, peripheral portions of the plastic film are welded to form an infusion bag, etc., the above-mentioned sealing layer (innermost layer) forms welded surfaces, and becomes an inner surface of a drug solution container to become a surface that directly contacts the drug solution. The plastic that forms the above-mentioned sealing layer (innermost layer) is thus required, for example, to be heat-sealable and be confirmed in terms of safety with respect to the drug solution.

Polyolefin-based plastics can be cited as specific examples of the plastic for forming the above-mentioned sealing layer (innermost layer).

Examples of polyolefin-based plastics include polyethylene (ethylene homopolymer), ethylene-α-olefin copolymers, polypropylene (propylene homopolymer), propylene-α-olefin random copolymers, and propylene-α-olefin block copolymers. Examples of the α-olefin of the above-mentioned ethylene-α-olefin copolymers include propylene, 1-butene, 1-pentene, 1-hexene, 4-methyl-1-pentene and other α-olefins with three to six carbons, and examples of the α-olefin of the above-mentioned propylene-α-olefin random copolymers and propylene-α-olefin block copolymers include ethylene and 1-butene, 1-pentene, 1-hexene, 4-methyl-1-pentene and other α-olefins with four to six carbons.

Among the examples given above, polyethylene, polypropylene, and mixed resins of these can be cited as being preferable as the polyolefin-based plastic used in the sealing layer.

In a case of, for example, preparing a bag-like drug solution container having a plurality of container chambers (so-called multiple-chamber bag) that are partitioned by barriers with an easily peeling property (easily peelable sealing portions), the sealing layer is preferably formed of a plastic made of a mixed resin of polyethylene and polypropylene to facilitate forming of the easily peelable sealing portions.

The above-mentioned protective layer (outermost layer) is a layer that forms an outer surface of the plastic drug solution container. The plastic that forms the above-mentioned protective layer (outermost layer) is thus selected as suited, for example, from the standpoint of preventing the intermediate layer formed of the above-mentioned polyol-based plastic, from being affected directly by moisture and from the standpoint of being able to maintain a predetermined strength according to a shape, application, etc. of the drug solution container during steam sterilization or hot water sterilization.

The above-mentioned protective layer (outermost layer) or the entirety of layers of the above-mentioned multilayer film that are disposed at the outer surface side of the plastic drug solution container with respect to the above-mentioned intermediate layer is required to prevent the intermediate layer, formed of the above-mentioned polyol-based plastic, from being directly affected by moisture and yet to have a water vapor transmission rate of some degree in order to provide the actions and effects of the present invention. Though the water vapor transmission rate of the protective layer (or the entirety of layers of the above-mentioned multilayer film that are disposed at the outer surface side of the plastic drug solution container with respect to the above-mentioned intermediate layer) is not restricted in particular, the water vapor transmission rate at a temperature of 25° C. and a humidity of 90% RH is preferably 1 to 50 g/m$^2$·24 h, more preferably 3 to 30 g/m$^2$·24 h, and even more preferably 3 to 10 g/m$^2$·24 h.

The above-mentioned water vapor transmission rate is measured according to A method (Humidity sensor method) defined in JIS K $7129_{-1992}$, "Testing Methods for water vapor transmission rate (instrument method) of Plastic Film and Sheeting."

Specific examples of the plastic for forming the above-mentioned protective layer (outermost layer) include polyolefin-based, polyamide-based, and polyester-based plastics. As examples of the above-mentioned polyolefin-based plastic, the same plastics given as examples above can be cited. Nylons such as nylon-6, nylon-6,6, and nylon-6,10 can be cited as examples of the above-mentioned polyamide-based plastic. Polyethylene terephthalate, polybutylene terephthalate, etc., can be cited as examples of the above-mentioned polyester-based plastic.

In the case where the plastic that forms the plastic drug solution container is a multilayer film, the multilayer film with the three-layer structure having, as mentioned above, the sealing layer formed of the polyolefin-based plastic as the innermost layer that makes up the inner surface side of the plastic drug solution container, the protective layer as the outermost layer that makes up the outer surface side of the plastic drug solution container, and the intermediate layer formed of the polyol-based plastic between the above-mentioned sealing layer and the above-mentioned protective layer can be cited as a specific embodiment.

Preferably, the above-mentioned multilayer film has furthermore a low water absorption layer, formed of a low water absorption plastic, at the inner surface side (sealing layer side) of the plastic drug solution container with respect to the above-mentioned intermediate layer. In this case, the intermediate layer formed of the above-mentioned polyol-based plastic can be made less likely affected by the water content in the drug solution.

Examples of the above-mentioned low water absorption plastic include cyclo olefin polymers, etc.

A cyclo olefin polymer has an extremely low water absorption rate, specifically of not more than 0.01%, and is thus favorable for lessening the effects of moisture on the intermediate layer formed of the polyol-based plastic.

The above-mentioned water absorption rate is measured in accordance with Method B (water absorption after immersion in boiling water) defined in JIS K $7209_{-2000}$ "Plastics—Determination of water absorption."

Specific examples of cyclo olefin polymers include such cyclo olefin polymers as copolymers (and hydrogenates thereof) of ethylene and dicyclopentadiene-based compounds, copolymers (and hydrogenates thereof) of ethylene and norbornene-based compounds, ring-opened polymers (and hydrogenates thereof) of cyclopentadiene-based compounds, and ring-opened copolymers formed of two or more types of cyclopentadiene compounds (and hydrogenates thereof).

The above-mentioned multilayer film may furthermore be provided with a layer formed of a plastic containing an elastomer for the purpose of adding pliability, transparency, and impact resistance to the plastic drug solution container.

Examples of the above-mentioned elastomer include polyolefin-based elastomers such as polyethylene-based elastomers and polypropylene-based elastomers, and other, and styrene-based elastomers such as styrene-ethylene/butylene-styrene block copolymers (SEBS), styrene-butadiene-styrene block copolymers (SBS), styrene-isoprene-styrene block copolymers (SIS), modified SEBS modified by maleic acid, etc., styrene-ethylene/propylene-styrene block copolymers (SEPS), styrene-ethylene/butylene block copolymers (SEB) and styrene-ethylene/propylene block copolymers (SEP). Among these, polyethylene-based elastomers can be cited as preferable examples.

Though not restricted thereto, plastics formed to a film form by an extrusion method such as the T-die method, inflation method, etc. can be cited as examples of the plastic that forms the plastic drug solution container. By forming the above-described drug solution container using such a plastic film, a plastic drug solution container with excellent flexibility and pliability can be formed.

Figure 2:
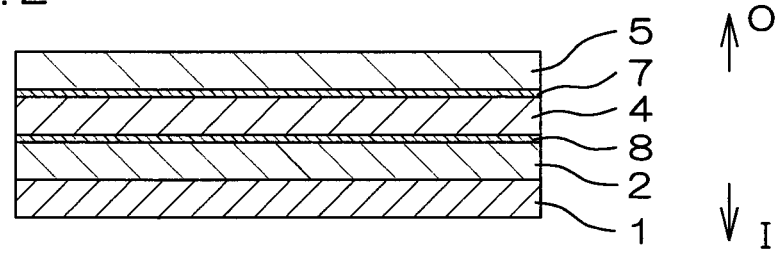
FIG. 2 is a schematic sectional view of another embodiment of a plastic that forms a plastic drug solution container.
Figure 3:
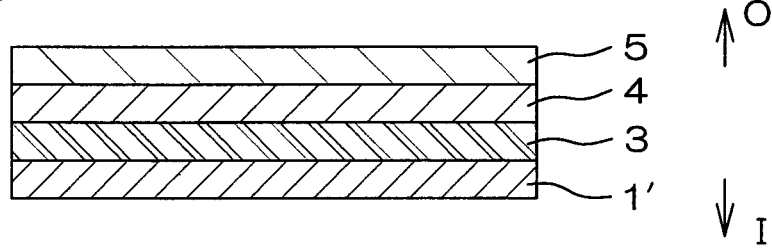
FIG. 3 is a schematic sectional view of yet another embodiment of a plastic that forms a plastic drug solution container.

FIGS. 1 to 3 are schematic sectional views of preferred embodiments of layer arrangements of the multilayer film in cases where the plastic forming the plastic drug solution container is the multilayer film. Though this invention is not restricted thereto, preferred embodiments include, for example:
(I) a multilayer film with a seven-layer structure having, in the order from an innermost layer making up an inner surface side I of a plastic drug solution container to an outermost layer making up an outer surface side O of a plastic drug solution container, a sealing layer 1 formed of a mixed resin of polyethylene and polypropylene, a layer 2 formed of polyethylene, a low water absorption layer 3 formed of a cyclo olefin polymer, an intermediate layer 4 formed of an ethylene-vinyl alcohol copolymer, and a protective layer 5 formed of polyethylene, and further having adherent layers 6 and 7 each formed of an adherent resin (for example, an adherent polyolefin, etc.) and disposed between the low water absorption layer 3 and the intermediate layer 4 and between the intermediate layer 4 and the protective layer 5, respectively (see FIG. 1);
(II) a multilayer film with a six-layer structure having, in the order from the innermost layer making up an inner surface side I of the plastic drug solution container to the outermost layer making up an outer surface side O of the plastic drug solution container, sealing layer 1 formed of a mixed resin of polyethylene and polypropylene, layer 2 formed of polyethylene, an intermediate layer 4 formed of an ethylene-vinyl alcohol copolymer, and a protective layer 5 formed of polyethylene, and further having adherent layers 8 and 7 each formed of an adherent resin (for example, an adherent polyolefin, etc.) and disposed between the layer 2 formed of polyethylene and the intermediate layer 4 and between the intermediate layer 4 and the protective layer 5, respectively (see FIG. 2); and
(III) a multilayer film with a four-layer structure having, in the order from the innermost layer making up an inner surface side I of the plastic drug solution container to the outermost layer making up an outer surface side O of the plastic drug solution container, a sealing layer 1' formed of polyethylene, a low water absorption layer 3 formed of a cyclo olefin polymer, an intermediate layer 4 formed of an ethylene-vinyl alcohol copolymer, and a protective layer 5 formed of polyethylene (see FIG. 3).

With the multilayer film described above in (III), adhesion of the low water absorption layer 3 with the intermediate layer 4 and the intermediate layer 4 with the protective layer 5 can be accomplished by applying an adhesive agent between the respective layers. Or, adherent layers formed of an adherent resin may be interposed in the same manner as in the multilayer films described in (I) and (II) above. Meanwhile, in the multilayer films described in (I) and (II) above, adhesion of the low water absorption layer 3 with the intermediate layer 4 and the intermediate layer 4 with the protective layer 5 can be accomplished by simply applying an adhesive agent without interposing the adhesion layers (6, 7, and 8) between the respective layers.

In the above-described multilayer films, the thickness of the respective layers is not restricted in particular and may be set such that, as one plastic drug solution container, the oxygen gas transmission rate after steam sterilization or hot water sterilization and the oxygen gas transmission rate in the steady state satisfy the ranges given above.

When the plastic drug solution container is formed, for example, as a pliable drug solution bag, preferably, the thickness of the above-mentioned intermediate layer is set to 3 to 20 μm and the thickness of the entirety of the multilayer film is set to approximately 180 to 300 μm.

The form of the plastic drug solution container is not restricted in particular and may, for example, be a bag-like drug solution container with excellent flexibility and pliability such as an infusion bag as mentioned above (see FIG. 4), or may be a drug solution container, such as an infusion bottle, that has a strength to maintain the container shape on its own while having flexibility and pliability. The above-mentioned bag-like drug solution container such as an infusion bag may be a single-chamber drug solution bag or a so-called multiple-chamber bag having a plurality of container chambers partitioned by easily peelable sealing portions.

Methods for forming such infusion bags, infusion bottles, etc. are not restricted in particular, and various methods, such as lamination, coextrusion, etc., may be selected and used as suited according to a form of the drug solution container.

In the drug solution container package according to this invention, a drug solution contained in the plastic drug solution container is not restricted in particular, and various drug solutions can be cited as examples. In particular, because in the above-described plastic drug solution container, the entry of oxygen from the exterior is restrained under a normal environment in which the drug solution container is used and because the oxygen remaining in the head space and the dissolved oxygen in the drug solution are removed with time due to the drug solution container being contained and sealed after steam sterilization or hot water sterilization along with the oxygen scavenger in the outer pouch having the oxygen barrier property, an infusion, especially an infusion containing a readily oxidized substance such as L-cysteine, L-tryptophan, fat, vitamin A, vitamin $B_1$, or vitamin C, is favorable as a drug solution to be contained in the plastic drug solution container.

In the drug solution container package according to this invention, the outer pouch, having an oxygen barrier property, has an oxygen gas transmission rate of preferably not more than 0.5 $cm^3/m^2 \cdot 24$ h·atm and more preferably not more than 0.1 $cm^3/24$ h·$m^2$·atm at a temperature of 25° C. and a humidity of 60% RH.

When the oxygen gas transmission rate of the outer pouch exceeds the above-mentioned range, it becomes difficult to obtain the effect of ex-post removal of the oxygen remaining in the head space of the plastic drug solution container and the dissolved oxygen in the drug solution.

Also, the outer pouch preferably has a water vapor transmitting property in some degree. In this case, moisture inside the outer pouch can be released to the exterior and the oxygen gas transmission rate of the plastic drug solution container can be made to reach the steady state readily.

A preferable range of the water vapor transmission rate of the outer pouch is around 0.5 to 30 g/m$^2$·24 h, though this will depend on the combination with the oxygen barrier property.

The material for forming the outer pouch is not restricted in particular and examples thereof include:

a multilayer film having a melt adhesion layer, forming an inner surface of the outer pouch, and being formed of a heat-sealable plastic (for example, a polyolefin such as polyethylene, polypropylene, etc.) and an aluminum foil laminated onto an outer surface side of the outer pouch with respect to the melt adhesion layer; and a film comprising a vapor-deposited film, having the above-mentioned melt adhesion layer and a vapor-deposited film of an inorganic material (such as aluminum, etc.) or an inorganic oxide (such as alumina, etc.) formed on an outer surface side of the outer pouch with respect to the melt adhesion layer.

Examples of the inorganic oxide in the vapor-deposited film of inorganic oxide include alumina (aluminum oxide), silica (silicon oxide), magnesium oxide, and titanium oxide. Among these, alumina can be cited as a preferable example from the standpoint of transparency of the vapor-deposited film.

As a material for forming the outer pouch with a water vapor transmitting property of some degree, a multilayer film, in which a plastic layer formed of polyvinyl alcohol, polyvinylidene chloride or the like and having a suitable oxygen barrier property and water vapor transmitting property is laminated on the outer surface side of a melt adhesion layer, can be cited as an example.

A material forming the outer pouch of the above-mentioned examples may furthermore have light-blocking printing using an ink containing a colorant or an ultra violet absorber, on the outer surface side of the outer pouch, or may have a protective film formed of polyester or polyolefin, etc. on the outer surface side of the outer pouch.

In the drug solution container package according to this invention, the oxygen scavenger is not restricted in particular, and various oxygen scavengers can be cited as examples. Specifically, oxygen scavengers containing an iron compound such as iron hydroxide, iron oxide, iron carbide, etc. as the effective component, and oxygen scavengers using low-molecular-weight phenol and activated carbon can be cited as examples. Examples of commercially available oxygen scavengers include "Ageless (registered trademark)" made by Mitsubishi G as Chemical Company, Inc., "Modulan (registered trademark)" made by Nippon Kayaku Company, Inc., "Secule (trade name)" made by Nippon Soda Co., Ltd., and "Tamotsu (registered trademark)" made by Oji Kako, Co., Ltd.

The oxygen scavenger may, for example, be contained along with the steam-sterilized or hot-water-sterilized drug solution container in the above-mentioned outer pouch in a state that the oxygen scavenger is filled in a bag formed of a plastic film with a high oxygen gas transmission rate (such as a polyolefin film).

By the drug solution container package and the method for manufacturing the same according to this invention, a drug solution that even contains a readily oxidized substance, for example, can be preserved with stability and without oxidative degradation over a long time. Moreover, oxidative degradation of a drug solution can be prevented during use of a drug solution bag.

EXAMPLES

Though this invention shall now be described based on examples and comparative examples, this invention is not restricted by the following examples.

<Preparation of Plastic Drug Solution Container>

Respective components that make up plastics (multilayer films) for forming plastic drug solution containers are as follows.

PE(1): ethylene-1-butene copolymer [density: 0.940 g/cm$^3$, water vapor transmission rate: 7 g/m$^2$·24 h (25° C., 90% RH, 20 µm), tradename: "Ultzex (registered trademark) 4020B," made by Prime Polymer Co., Ltd.]

PE(2): mixture of 45 weight % of ethylene-1-butene copolymer [density: 0.920 g/cm$^3$, trade name: "Ultzex (registered trademark) 2010," made by Prime Polymer Co., Ltd.], 50 weight % of ethylene-1-butene copolymer [density: 0.885 g/cm$^3$, trade name: "Tafmer (registered trademark) A0585X," made by Prime Polymer Co., Ltd.], and 5 weight % of polyethylene homopolymer [density: 0.965 g/cm$^3$, trade name: "Hi-zex (registered trademark) 65150B," made by Prime Polymer Co., Ltd.]

EVOH(1): ethylene content: 27 mole %, trade name: "Eval (registered trademark) L101," made by Kuraray Co., Ltd.

EVOH(2): ethylene content: 44 mole %, trade name: "Eval (registered trademark) E105," made by Kuraray Co., Ltd.

COP: norbornene-based ring-opened polymer hydrogenate [water absorption percentage: less than 0.01%, trade name: "Zeonor (registered trademark) 1020R," made by Zeon Corporation]

PP: polypropylene (density: 0.900 g/cm$^3$, trade name: "B355," made by Prime Polymer Co., Ltd.)

NY: nylon-6 [trade name: "Amilan (registered trademark) CM1017," made by Toray Industries Inc.]

PE-PP: mixture of 85 weight % of the above-mentioned PE(1) and 15 weight % of polypropylene homopolymer (density: 0.910 g/cm$^3$, trade name: "J103WA," made by Prime Polymer Co., Ltd.)

adherent PE: unsaturated carboxylic acid modified polyethylene [density: 0.905 g/cm$^3$, water vapor transmission rate: 10 g/m$^2$·24 h (25° C., 90% RH, 20 µm), adherent polyolefin of the tradename: "Admer (registered trademark)," made by Prime Polymer Co., Ltd.]

PBT: polybutylene terephthalate [water vapor transmission rate: 23 g/m$^2$·24 h (25° C., 90% RH, 10 µm), made by Mitsubishi Engineering-Plastics Corporation]

Example 1

Figure 4:
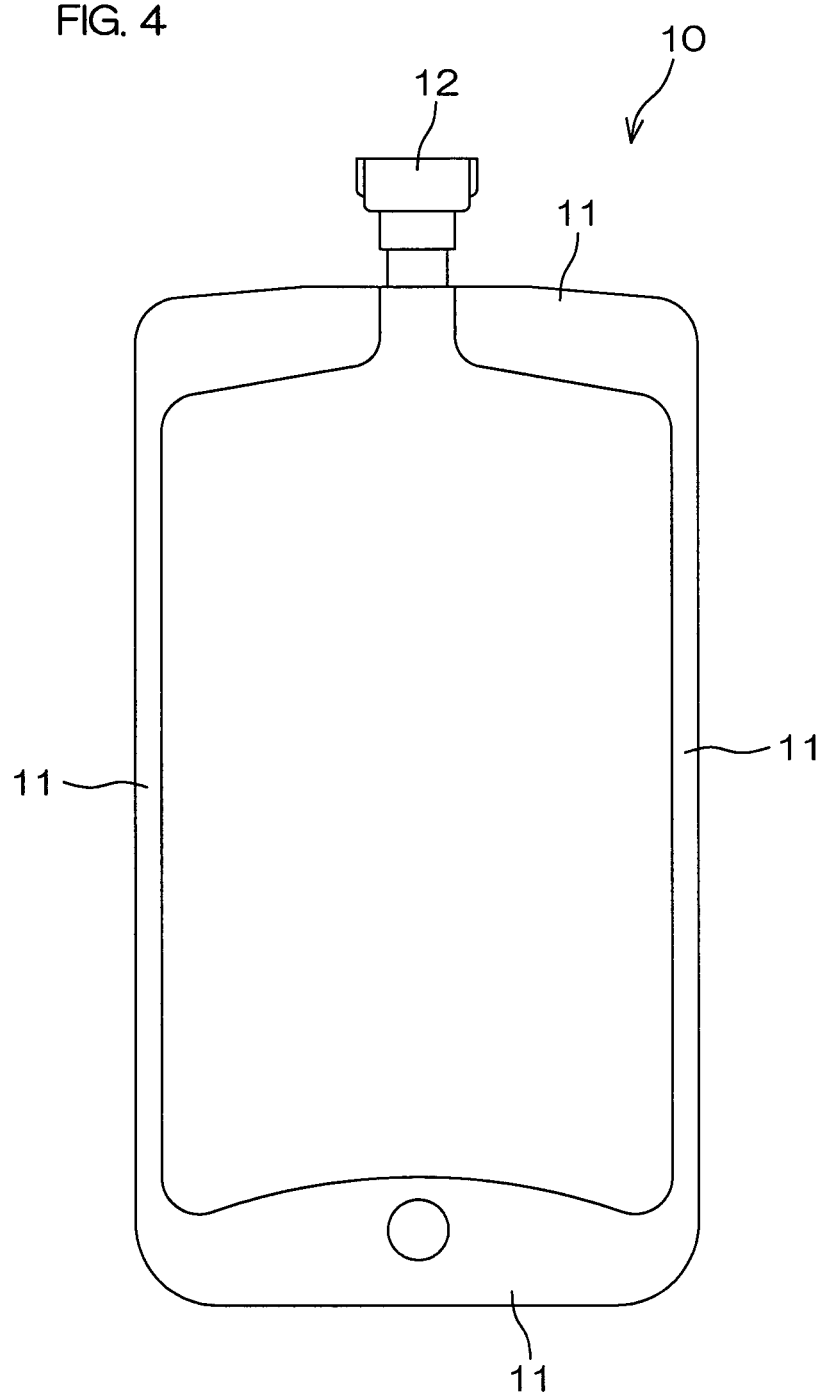
FIG. 4 is a front view of an embodiment of a drug solution bag.

Respective layers shown in Table 1 were coextrusion molded so as to be laminated in the order indicated in Table 1 to obtain a multilayer film for forming a drug solution bag (plastic drug solution container) 10 shown in FIG. 4. This multilayer film is a film with the seven-layer structure shown in FIG. 1. A water vapor transmission rate of a laminate, formed of a protective layer 5 and an adherent layer 7 of this multilayer film, was 4.1 g/m$^2$·24 h (25° C., 90% RH).

The two above-described multilayer films were then overlapped and peripheral portions 11 were heat sealed by a normal method to prepare the drug solution bag 10 shown in FIG. 4. A port-type mouth member, molded using the above-mentioned PE (1), was used as a mouth member 12.

Example 2

Respective layers shown in Table 1 were coextrusion molded so as to be laminated in the order indicated in Table 1 to obtain a multilayer film for forming a drug solution bag 10. This multilayer film is a film with the six-layer structure shown in FIG. 2.

Then, except for using two these multilayer films, the drug solution bag 10, shown in FIG. 4, was prepared in the same manner as Example 1.

Comparative Example 1

Respective layers shown in Table 1 were coextrusion molded so as to be laminated in the order indicated in Table 1 to obtain a multilayer film for forming a drug solution bag 10. This multilayer film is a film with a similar seven-layer structure as shown in FIG. 1.

Then, except for using two these multilayer films, the drug solution bag 10, shown in FIG. 4, was prepared in the same manner as Example 1.

Comparative Example 2

Respective layers shown in Table 1 were coextrusion molded so as to be laminated in the order indicated in Table 1 to obtain a multilayer film for forming a drug solution bag 10. This multilayer film is a film with a five-layer structure that does not have an adherent layer.

Then, except for using two these multilayer films, the drug solution bag 10, shown in FIG. 4, was prepared in the same manner as Example 1.

The layer arrangement of the drug solution bag 10 and oxygen gas transmission rates of the multilayer film forming the drug solution bag 10 are shown for each of Examples 1 and 2 and Comparative Examples 1 and 2 in Table 1.

TABLE 1

| | Example 1 | Example 2 | Comparative Example 1 | Comparative Example 2 |
|---|---|---|---|---|
| <Layer Arrangement of Multilayer Film> (Outer surface side O) | | | | |
| Protective layer | PE (1) (20 μm) | PE (1) (20 μm) | PE (1) (20 μm) | PE (1) (20 μm) |
| Adherent layer | Adherent PE (20 μm) | Adherent PE (20 μm) | Adherent PE (20 μm) | — |
| Intermediate layer | EVOH (1) (5 μm) | EVOH (2) (5 μm) | — | — |
| Other layer | — | — | NY (5 μm) | PE (2) (100 μm) |
| Adherent layer | Adherent PE (20 μm) | Adherent PE (20 μm) | Adherent PE (20 μm) | — |
| Low water absorption layer | COP (10 μm) | — | COP (10 μm) | — |
| Other layer | — | — | — | PP (10 μm) |
| Layer formed of polyethylene | PE (2) (145 (μm)) | PE (2) (155 μm) | PE (2) (145 μm) | PE (2) (100 μm) |
| Sealing layer | PE-PP (30 μm) | PE-PP (30 μm) | PE-PP (30 μm) | PE-PP (30 μm) |
| (Inner surface side I) <Total thickness of multilayer film> | | | | |
| | 250 μm | 250 μm | 250 μm | 260 μm |
| <Oxygen gas transmission rate> | | | | |
| Steady state | 5 | 20 | 270 | 900 |
| Six hours after sterilization | 800 | 800 | — | — |

* The numerical values in the parentheses in the "Layer Arrangement of Multilayer Film" column are the thicknesses of the respective layers.
* The unit of the oxygen gas transmission rate is $cm^3/m^2 \cdot 24\,h \cdot atm$.

<Evaluation Test of Plastic for Forming Plastic Drug Solution Container>

The multilayer film obtained in Example 1 was subjected to 30 minutes of high-pressure steam sterilization in a nitrogen atmosphere in a steam saturated state (temperature: 110° C., pressure: 2700 hPa) and thereafter subjected to water removal of a surface of the multilayer film by warm air of approximately 40° C. After the steam sterilization, the multilayer film was left standing for three weeks under an atmosphere of a temperature of 25° C. and a humidity of 60% RH to observe a variation with time of the oxygen gas transmission rate (temperature: 25° C., humidity: 60% RH). The product of the name "OX-TRAN (registered trademark)" made by MOCON, Inc. was used to measure the oxygen gas transmission rate.

Figure 5:
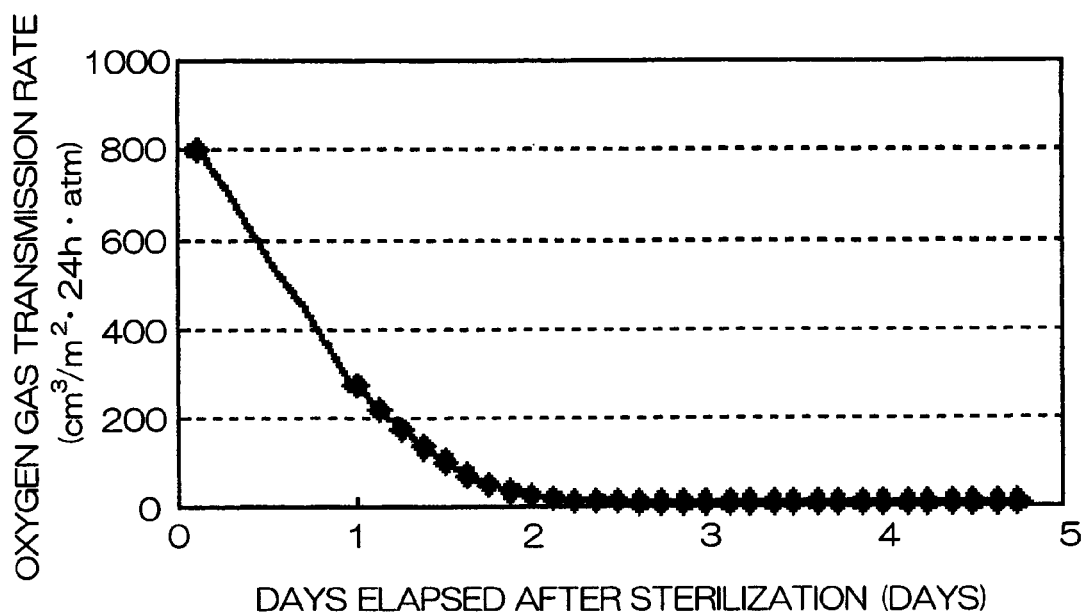
FIG. 5 is a graph of a variation with time of an oxygen gas transmission rate of a multilayer film obtained in Example 1.

FIG. 5 is a graph of results of measuring the variation with time of the oxygen gas transmission rate. As shown in FIG. 5, after the above-described steam sterilization approximately three days were required for the oxygen gas transmission rate (temperature: 25° C., humidity: 60% RH) of the multilayer film to reach the steady state.

<Preparation of Drug Solution Container Packages>

Each of the drug solution bags 10 prepared in Examples 1 and 2 and Comparative Examples 1 and 2 was filled with 300 mL of distilled water for injection and then sealed. A head space volume was set to approximately 30 mL and nitrogen replacement (approximately 50%) was performed so that the oxygen concentration of the head space became 10%.

The drug solution bag 10 was then set in an autoclave and subjected to high-pressure steam sterilization by heating for 30 minutes in a nitrogen atmosphere in a steam saturated state (temperature: 110° C., pressure: 2700 hPa). The oxygen concentration in this nitrogen atmosphere was adjusted to be not more than 2%.

After the high-pressure steam sterilization, water removal by blowing warm air of approximately 40° C. was performed to remove moisture from the outer surface of the each drug solution bag 10, and then the each drug solution bag 10 was contained and sealed, along with an oxygen scavenger [trade name: "Ageless (registered trademark)" made by Mitsubishi G as Chemical Co.], in an outer pouch to obtain a drug solution container package.

The above-mentioned outer pouch is a pouch formed of a multilayer film with a three-layer structure, in which an inner surface layer is formed of polyethylene, an intermediate layer is formed of polyvinyl alcohol, and an outer surface layer is formed of stretched polypropylene, and the oxygen gas transmission rate thereof at a temperature of 25° C. and a humidity of 60% RH was not more than 0.1 $cm^3/m^2 \cdot 24\,h \cdot atm$ and the water vapor transmission rate thereof at a temperature of 25° C. and a humidity of 90% RH was 0.5 $g/m^2 \cdot 24\,h$. The volume of the inner space of the outer pouch was set to approximately 300 to 500 mL and the oxygen concentration inside the outer pouch was adjusted to be not more than 2% by nitrogen replacement.

The time taken to make the drug solution bag contained and sealed in the outer pouch after the high-pressure steam sterilization was within one hour.

<Evaluation Test 1 of Drug Solution Container Packages>

Each of the drug solution container packages obtained in the above-described Examples 1 and 2 and Comparative Examples 1 and 2 was left standing under an environment of a temperature of 25° C. and a humidity of 60% RH, and on each day, the oxygen concentration in a content liquid was measured using a nondestructive oxygen concentration meter (trade name: "Fibox 3" made by PreSens GmbH).

Figure 6:
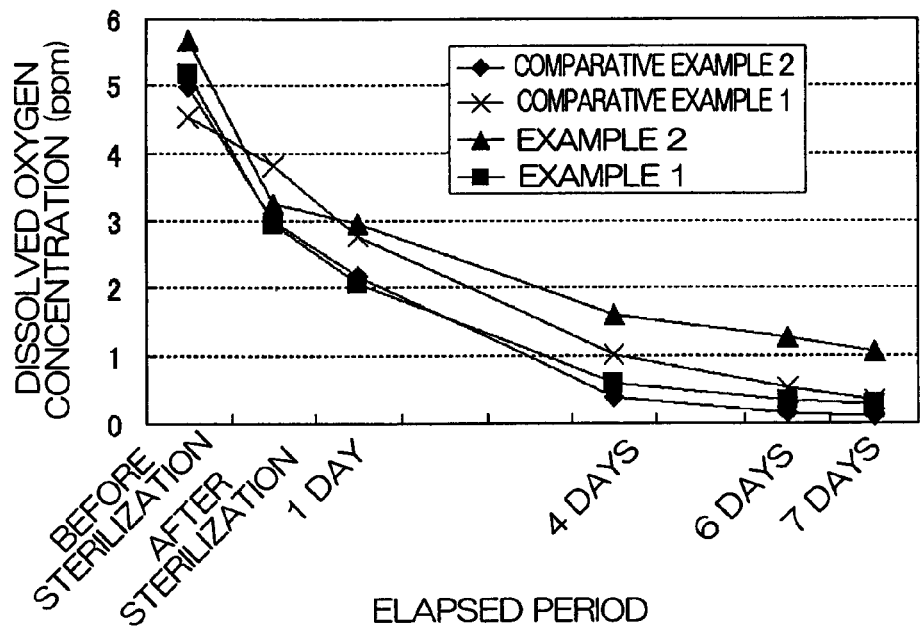
FIG. 6 is a graph of variations with time of dissolved oxygen concentrations in drug solution container packages obtained in Examples and Comparative Examples.

As a result, it was found as shown in FIG. 6 that, with respect to the all drug solution container packages of Examples 1 and 2 and Comparative Examples 1 and 2, the oxygen concentration in the content liquid can be reduced to not more than 1 ppm by the elapse of approximately seven days from containing and sealing in the outer pouch.

<Evaluation Test 2 of Drug Solution Container Packages>

Each of the drug solution container packages used in the above-described Evaluation Test 1 was further left standing for seven days from the preparation of the drug solution container package to bring the oxygen concentration in the content liquid close to 0 ppm. Then under an environment of a temperature of 25° C. and a humidity of 60% RH, the drug solution bag 10 was taken out from the outer pouch, and while leaving the bag under an environment of the temperature of 25° C. and humidity of 60% RH in a state of being hung on a hanging stand for an infusion bag, the oxygen concentration in the content liquid was measured using the nondestructive oxygen concentration meter (the above-mentioned "Fibox 3") at each predetermined time.

Figure 7:
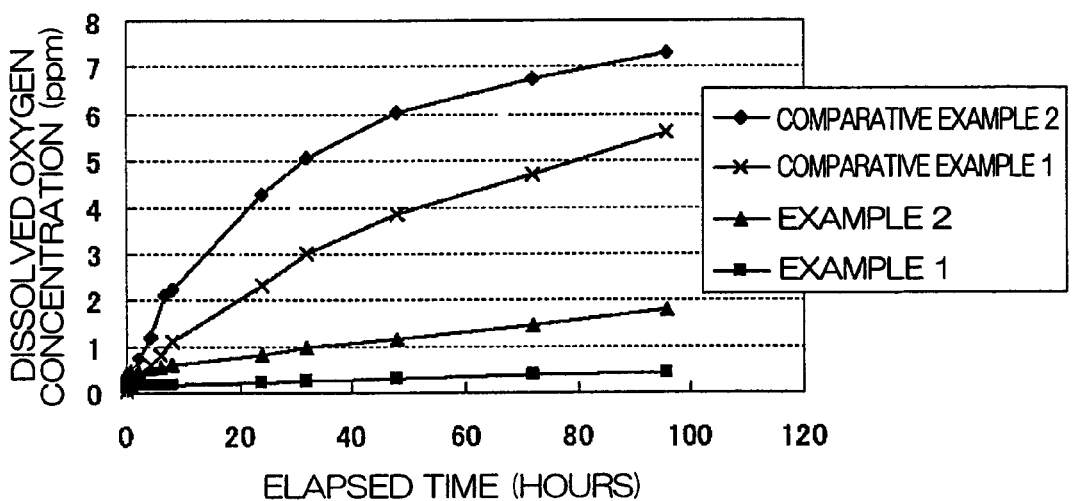
FIG. 7 is a graph of variations with time of dissolved oxygen concentrations in drug solution containers (drug solution bags) obtained in Examples and Comparative Examples.

As a result, in the drug solution bags of Examples 1 and 2, entry of oxygen into the content liquid could be restrained as much as possible as shown in FIG. 7 even after being taken out from the outer pouch. On the other hand, there was significant entry of oxygen in the drug solution bags of Comparative Example 1 and Comparative Example 2.

<Evaluation Test 3 of Drug Solution Container Packages>

Each of the drug solution container packages obtained in the above-described Example 1 (samples different from those used in Evaluation Tests 1 and 2) was left standing for various days under an environment of a temperature of 25° C. and a humidity of 60% RH, and with respect to each of the drug solution container packages thus prepared, the drug solution bag was taken out, and after cutting the film and wiping off moisture, the oxygen gas transmission rate of the film was measured using the product of the name "OX-TRAN (registered trademark)" made by MOCON, Inc. The results are shown in FIG. 8.

Figure 8:
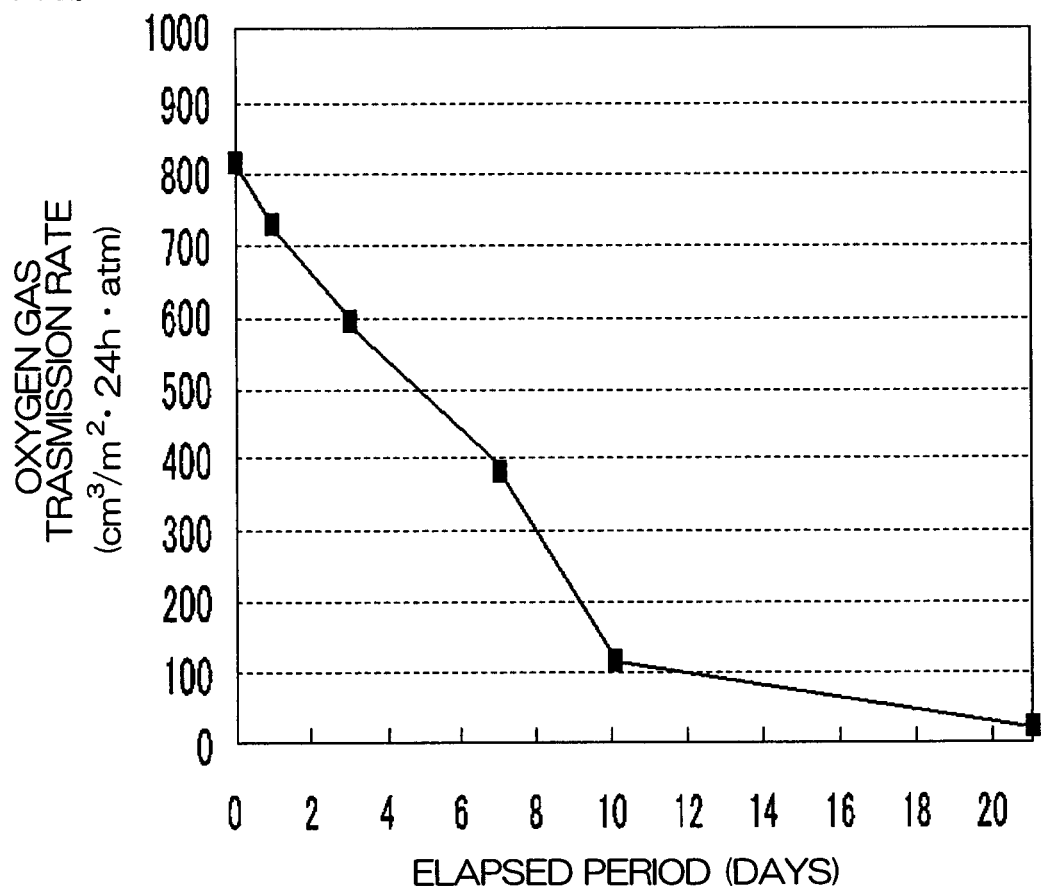
FIG. 8 is a graph of a variation with time of an oxygen gas transmission rate of the multilayer film obtained in Example 1 in the state of being contained in an outer pouch.

As shown in FIG. 8, by being packed in the outer pouch, the multilayer film exhibited a high oxygen gas transmission rate (temperature: 25° C., humidity: 60% RH) for approximately three to four days after high-pressure steam sterilization. It was also found that after steam sterilization approximately ten days are required for the oxygen gas transmission rate to reach the steady state. The oxygen in the drug solution bag 10 could thus be adequately absorbed by the oxygen scavenger before the oxygen gas transmission rate returned to the steady state after steam sterilization.

<Preparation of Plastic Drug Solution Containers>

Example 3

Using the plastics cited above as examples, respective layers shown in Table 2 were coextrusion molded so as to be laminated in the order indicated in Table 2 to obtain a multilayer film for forming a drug solution bag (plastic drug solution container) 10 shown in FIG. 4. This multilayer film is a film with the seven-layer structure shown in FIG. 1. The water vapor transmission rate of a laminate, formed of a protective layer 5 and an adherent layer 7 of this multilayer film, was 4.1 g/m$^2$·24 h (25° C., 90% RH).

The two above-described multilayer films were then overlapped and their peripheral portions 11 were heat sealed by a normal method to prepare a drug solution bag 10 shown in FIG. 4. A port-type mouth member, molded using the above-mentioned PE(1), was used as a mouth member 12.

Example 4

Respective layers shown in Table 2 were coextrusion molded so as to be laminated in the order indicated in Table 2 to obtain a multilayer film for forming a drug solution bag 10. This multilayer film is a film with the seven-layer structure shown in FIG. 1. The water vapor transmission rate of a laminate, formed of a protective layer 5 and an adherent layer 7 of this multilayer film, was 7.0 g/m$^2$·24 h (25° C., 90% RH).

Then, except for using two these multilayer films, the drug solution bag 10, shown in FIG. 4, was prepared in the same manner as Example 3.

Example 5

Respective layers shown in Table 2 were coextrusion molded so as to be laminated in the order indicated in Table 2 to obtain a multilayer film for forming a drug solution bag 10. This multilayer film is a film with the six-layer structure shown in FIG. 2. The water vapor transmission rate of the laminate, formed of a protective layer 5 and an adherent layer 7 of this multilayer film, was 5.1 g/m$^2$·24 h (25° C., 90% RH).

Then, except for using two these multilayer films, the drug solution bag 10, shown in FIG. 4, was prepared in the same manner as Example 3.

Example 6

Respective layers shown in Table 2 were coextrusion molded so as to be laminated in the order indicated in Table 2 to obtain a multilayer film for forming a drug solution bag 10. This multilayer film is a film with the seven-layer structure shown in FIG. 1. The water vapor transmission rate of a laminate, formed of a protective layer 5 and an adherent layer 7 of this multilayer film, was 3.2 g/m$^2$·24 h (25° C., 90% RH).

Then, except for using two of these multilayer films, the drug solution bag 10, shown in FIG. 4, was prepared in the same manner as Example 3.

The layer arrangement of the drug solution bag 10 and the oxygen gas transmission rates of the multilayer film that forms the drug solution bag 10 are shown for each of Examples to 6 in Table 2.

TABLE 2

|  | Example 3 | Example 4 | Example 5 | Example 6 |
| --- | --- | --- | --- | --- |
| <Layer Arrangement of Multilayer Film> (Outer surface side O) | | | | |
| Protective layer | PE (1) (20 μm) | PBT (1) (10 μm) | PE (1) (16 μm) | PE (1) (30 μm) |
| Adherent layer | Adherent PE (20 μm) | Adherent PE (20 μm) | Adherent PE (16 μm) | Adherent PE (20 μm) |
| Intermediate layer | EVOH (1) (15 μm) | EVOH (1) (5 μm) | EVOH (1) (4 μm) | EVOH (1) (5 μm) |
| Adherent layer | Adherent PE (20 μm) | Adherent PE (20 μm) | Adherent PE (16 μm) | Adherent PE (20 μm) |

TABLE 2-continued

|  | Example 3 | Example 4 | Example 5 | Example 6 |
|---|---|---|---|---|
| Low water absorption layer | COP (10 μm) | COP (10 μm) | — | COP (10 μm) |
| Layer formed of polyethylene | PE (2) (130 μm) | PE (2) (155 μm) | PE (2) (124 μm) | PE (2) (175 μm) |
| Sealing layer | PE-PP (30 μm) | PE-PP (30 μm) | PE-PP (24 μm) | PE-PP (40 μm) |
| | (Inner surface side I) | | | |
| | <Water vapor transmission rate of protective layer + adhesive layer> | | | |
| | 4.1 | 7.0 | 5.1 | 3.2 |
| | <Total thickness of multilayer film> | | | |
| | 250 μm | 250 μm | 200 μm | 300 μm |
| | <Oxygen gas transmission rate> | | | |
| Steady state | 1 | 5 | 25 | 5 |
| Six hours after Sterilization | 500 | 200 | 1000 | 500 |

* The numerical values in the parentheses in the "Layer Arrangement of Multilayer Film" column are the thicknesses of the respective layers.
* The unit of the oxygen gas transmission rate is $cm^3/m^2 \cdot 24\ h \cdot atm$.
* The unit of the water vapor transmission rate is $g/m^2 \cdot 24\ h$.

<Preparation of Drug Solution Container Packages>

Each of the drug solution bags 10 prepared in Examples 3 to 6 was filled with 300 mL of distilled water for injection and then sealed. A head space volume was set to approximately 30 mL and nitrogen replacement (approximately 50%) was performed so that an oxygen concentration of the head space became 10%.

The each drug solution bag 10 was then set in an autoclave and subjected to high-pressure steam sterilization by heating for 30 minutes in a nitrogen atmosphere in a steam saturated state (temperature: 110° C., pressure: 2700 hPa). The oxygen concentration in this nitrogen atmosphere was adjusted to be not more than 2%.

After the high-pressure steam sterilization, water removal by blowing warm air of approximately 40° C. was performed for a minute to remove moisture from the outer surface of the each drug solution bag 10, and then the each drug solution bag 10 was contained and sealed, along with an oxygen scavenger (trade name: "Ageless (registered trademark)," made by Mitsubishi Gas Chemical Co.), in an outer pouch to obtain a drug solution container.

In each of Examples 3, 5, and 6, a pouch, formed of a multilayer film with a three-layer structure in which an inner surface layer is formed of polyethylene, an intermediate layer is formed of polyvinyl alcohol, an outer surface layer is formed of stretched polypropylene, the oxygen gas transmission rate at a temperature of 25° C. and a humidity of 60% RH was not more than 0.1 $cm^3/m^2 \cdot 24\ h \cdot atm$, and the water vapor transmission rate at a temperature of 25° C. and a humidity of 90% RH was 0.5 $g/m^2 \cdot 24\ h$, was used as the above-mentioned outer pouch.

On the other hand, in Example 4, a pouch, formed of a multilayer film with a three-layer structure in which an intermediate layer is formed of an ethylene-vinyl alcohol copolymer, inner and outer layers are formed of polyethylene, the oxygen gas transmission rate at a temperature of 25° C. and a humidity of 60% RH was 0.5 $cm^3/m^2 \cdot 24\ h \cdot atm$, and the oxygen gas transmission rate at a temperature of 25° C. and a humidity of 90% RH was 3 $cm^3/m^2 \cdot 24\ h \cdot atm$, was used as the outer pouch.

The volume of the inner space of each of the above-described outer pouches was set to approximately 300 to 500 mL and the oxygen concentration inside the outer pouch was adjusted to be not more than 2% by nitrogen replacement.

<Evaluation Tests of Drug Solution Container Packages>

When carrying out the same test as the above-described Evaluation Test 1 on each of the drug solution container packages obtained in the above-described Examples 3 to 6, it was found that, in all the cases, the oxygen concentration in the content liquid could be reduced to not more than 1 ppm by the elapse of approximately seven days from containing and sealing in the outer pouch.

When carrying out the same test as the above-described Evaluation Test 2, it was found that in each of Examples 3, 4, and 6, the oxygen concentration in the content liquid was less than 0.5 ppm after 96 hours (four days) from being taken out of the outer pouch and that entry of oxygen into a content liquid was thus restrained as much as possible. Meanwhile, in Example 5, it was found that the oxygen concentration in the content liquid was less than 2 ppm after 72 hours (three days) after being taken out of the outer pouch and that entry of oxygen into a content liquid was within an adequately allowable range.

Though in the above description the present invention is provided in the form of exemplary embodiments of the invention, these are simply examples and should not be interpreted as restricting the invention. Modifications of this invention that are obvious to those skilled in the art are included within the scope of the Claims provided below.

Industrial Applicability

By the drug solution container package and the method for manufacturing the same according to this invention, oxidative degradation of a drug solution contained in a drug solution container can be restrained in a high degree. This invention is thus favorable for applications of medical containers, such as drug solution containers and infusion containers, and is particularly favorable for applications of medical containers containing a drug solution, etc. that contains a readily oxidized substance.

The invention claimed is:

1. A drug solution container package comprising: a plastic drug solution container containing a drug solution, the container being sealed and sterilized by steam or hot water; an oxygen scavenger; and an outer pouch having an oxygen barrier property for containing and sealing the plastic drug solution container and the oxygen scavenger,
   wherein a plastic forming the plastic drug solution container has an oxygen gas transmission rate of not less than 200 $cm^3/m^2 \cdot 24\ h \cdot atm$ at a temperature of 25° C. and a humidity of 60% RH within twelve hours after being subjected to steam sterilization or hot water sterilization, and has an oxygen gas transmission rate of not more than 100 $cm^3/m^2 \cdot 24\ h \cdot atm$ at a temperature of 25° C. and a humidity of 60% RH when the oxygen gas transmission rate is in a steady state,
   wherein the plastic forming the plastic drug solution container is a multilayer film having a sealing layer at an inner surface side of the plastic drug solution container, a protective layer on an outer surface side of the plastic drug solution container, and an intermediate layer between the sealing layer and the protective layer,
   wherein the intermediate layer is formed from a polyol-based plastic and
   wherein the multilayer film includes a low water absorption layer, formed of a low water absorption plastic having a water absorption rate of not more than 0.01%, between the sealing layer and the intermediate layer.

2. The drug solution container package according to claim 1, wherein the steam sterilization is a process of heating the plastic drug solution container for 10 to 60 minutes under an inert gas atmosphere at a temperature of 100 to 121° C. and in a steam saturated state.

3. The drug solution container package according to claim 1, wherein the polyol-based plastic of the intermediate layer is an ethylene-vinyl alcohol copolymer with an ethylene content of 10 to 45 mole %.

4. The drug solution container package according to claim 1, wherein, of the multilayer film, a water vapor transmission rate of the entirety of layers disposed at the outer surface side of the plastic drug solution container with respect to the intermediate layer is 1 to 50 g/m$^2$·24 h at a temperature of 25° C. and a humidity of 90% RH.

5. The drug solution container package according to claim 1, wherein the low water absorption plastic is a cyclo olefin polymer.

6. The drug solution container package according to claim 1, wherein the plastic forming the plastic drug solution container has an oxygen gas transmission rate of 500 to 1000 cm$^3$/m$^2$·24 h·atm at a temperature of 25° C. and a humidity 60% RH within twelve hours after being subjected to steam sterilization or hot water sterilization.

7. The drug solution container package according to claim 1, wherein the plastic forming the plastic drug solution container has an oxygen gas transmission rate of 0.5 to 70 cm$^3$/m$^2$·24 h·atm at a temperature of 25° C. and a humidity of 60% RH when the oxygen gas transmission rate is in a steady state.

8. The drug solution container package according to claim 1, wherein the plastic drug solution container is formed of a plastic that requires at least two days for the oxygen gas transmission rate to attain the steady state after steam sterilization or hot water sterilization.

9. The drug solution container package according to claim 1, wherein the drug solution contained and sealed in the plastic drug solution container is a drug solution that contains an oxidizable substance.

10. The drug solution container package according to claim 1, wherein the outer pouch has a water vapor transmission rate of 0.5 to 30 g/m$^2$·24 h at a temperature of 25° C. and a humidity of 90% RH.

11. A method for manufacturing a plastic drug solution container package, wherein plastic forming the plastic drug solution container is a multilayer film having a sealing layer at an inner surface side of the plastic drug solution container, a protective layer on an outer surface side of the plastic drug solution container, and an intermediate layer between the sealing layer and the protective layer, wherein the multilayer film includes a low water absorption layer, formed of a low water absorption plastic having a water absorption rate of not more than 0.01%, between the sealing layer and the intermediate layer, and wherein after making a drug solution contained and sealed in the plastic drug solution container formed of the plastic, which has an oxygen gas transmission rate of not less than 200 cm$^3$/m$^2$·24 h·atm at a temperature of 25° C. and a humidity of 60% RH within twelve hours after being subjected to steam sterilization or hot water sterilization and oxygen gas transmission rate of not more than 100 cm$^3$/m$^2$·24 h·atm at a temperature of 25° C. and a humidity of 60% RH when the oxygen gas transmission rate is in a steady state, the plastic drug solution container is steam sterilized or hot water sterilized, and then the sterilized plastic drug solution container and an oxygen scavenger are contained and sealed in an outer pouch having an oxygen barrier property to form a plastic drug solution container package, wherein the intermediate layer is formed from a polyol-based plastic.

12. The method for manufacturing a drug solution container package according to claim 11, wherein the steam sterilization is a process of heating the plastic drug solution container for 10 to 60 minutes under an inert gas atmosphere at a temperature of 100 to 121° C. in a steam saturated state.

13. The method for manufacturing a drug solution container package according to claim 11, wherein the outer pouch has a water vapor transmission rate of 0.5 to 30 g/m$^2$·24 h at a temperature of 25° C. and a humidity of 90% RH.

14. The method for manufacturing a drug solution container package according to claim 11, wherein before the plastic drug solution container and the oxygen scavenger are contained and sealed in the outer pouch, a space between the plastic drug solution container and the outer pouch is filled with an inert gas.

* * * * *